United States Patent
Vogel et al.

(10) Patent No.: US 9,673,471 B2
(45) Date of Patent: Jun. 6, 2017

(54) PRODUCTION OF A BIOFILM ON AN ELECTRODE FOR A BIOCELL, ELECTRODE AND BIOCELL OBTAINED

(75) Inventors: Timothy Vogel, Lyons (FR);
Jean-Michel Monier, Neuville sur Saone (FR); Naoufel Haddour, Villeurbanne (FR)

(73) Assignees: CENTRE NATIONAL DE LA RECHERCHE SCIENTIFIQUE (C.N.R.S.), Paris (FR); UNIVERSITE CLAUDE BERNARD LYON 1, Villeurbanne (FR); ECOLE CENTRALE DE LYON, Ecully (FR)

( * ) Notice: Subject to any disclaimer, the term of this patent is extended or adjusted under 35 U.S.C. 154(b) by 274 days.

(21) Appl. No.: 12/994,786

(22) PCT Filed: May 27, 2009

(86) PCT No.: PCT/FR2009/050990
§ 371 (c)(1),
(2), (4) Date: Feb. 4, 2011

(87) PCT Pub. No.: WO2009/153499
PCT Pub. Date: Dec. 23, 2009

(65) Prior Publication Data
US 2011/0123876 A1 May 26, 2011

(30) Foreign Application Priority Data
May 27, 2008 (FR) ...................................... 08 53441

(51) Int. Cl.
*H01M 8/16* (2006.01)
*C12M 1/12* (2006.01)
(Continued)

(52) U.S. Cl.
CPC ................. *H01M 8/16* (2013.01); *C02F 3/00* (2013.01); *C02F 11/00* (2013.01); *C12M 25/08* (2013.01);
(Continued)

(58) Field of Classification Search
CPC . H01M 8/16; H01M 4/04; Y02P 70/56; Y02E 60/527; C12M 25/08; C02F 3/00; C02F 11/00
(Continued)

(56) References Cited

U.S. PATENT DOCUMENTS 7,491,453 B2  2/2009  Logan et al.
7,709,113 B2  5/2010  Logan et al.
(Continued)

FOREIGN PATENT DOCUMENTS

DE          1902672         9/1970
DE       DE 19 02 672      9/1970
WO    WO 2005005981 A2 *  1/2005

OTHER PUBLICATIONS

"Power boosted 10-fold in microbial cell", Fuel Cell Bull., 2006, 8, 7-8.*
(Continued)

*Primary Examiner* — Alex Usyatinsky
(74) *Attorney, Agent, or Firm* — B. Aaron Schulman, Esq.; Stites & Harbison, PLLC.

(57) ABSTRACT

A method for the production of a biofilm at the surface of an electrode in a liquid medium containing bacteria and a substrate for growth of the bacteria, in which a system of electrodes constituted of two electrodes, which are connected to a direct electric current source, is used, these two electrodes are placed in the medium and a predetermined and constant potential difference is applied between the
(Continued)

electrodes, by virtue of which biofilms form at the surface of the electrodes. Resulting electrodes and biocells.

15 Claims, 3 Drawing Sheets

(51) Int. Cl.
  *C02F 11/00* (2006.01)
  *C02F 3/00* (2006.01)
  *H01M 8/04* (2016.01)

(52) U.S. Cl.
  CPC .............. *H01M 8/04* (2013.01); *Y02E 60/527* (2013.01); *Y02P 70/56* (2015.11)

(58) Field of Classification Search
  USPC ................... 429/2, 401, 253; 435/252.1, 243
  See application file for complete search history.

(56) References Cited

U.S. PATENT DOCUMENTS

| | | |
|---|---|---|
| 2005/0164331 A1 | 7/2005 | Kim et al. |
| 2006/0147763 A1 | 7/2006 | Angenent et al. |
| 2006/0234110 A1* | 10/2006 | Bergel .............................. 429/43 |
| 2007/0134520 A1* | 6/2007 | Shimomura et al. ............. 429/2 |
| 2007/0259216 A1 | 11/2007 | Logan et al. |
| 2007/0259217 A1 | 11/2007 | Logan et al. |
| 2008/0090736 A1 | 4/2008 | Zhao et al. |
| 2008/0124585 A1 | 5/2008 | Schilling |
| 2008/0277273 A1 | 11/2008 | Logan |
| 2008/0286624 A1* | 11/2008 | Lovley et al. .................. 429/27 |
| 2008/0292912 A1 | 11/2008 | Logan et al. |
| 2010/0119920 A1 | 5/2010 | Logan et al. |
| 2010/0151279 A1 | 6/2010 | Logan et al. |
| 2010/0178530 A1* | 7/2010 | Min et al. ......................... 429/2 |
| 2010/0227203 A1* | 9/2010 | Ter Heijne et al. .............. 429/2 |

OTHER PUBLICATIONS

Reguera, G. et al."Biofilm and nanowire production lead to increased current in Geobacter sulfurreducen Fuel Cell", Applied and Enviromental Microbiology, 2006,7345-7348.*
Logan, B., L. et al., "Increased performance of single-chamber microbial fuel cell using an improved cathode structure", Electrochemistry Communications, 2006, 8, 489-494.*
Marsili) et al "Direct Electrochemical Characterization of Catalytic Electrode-Attached Biofilms" Applied and Environmental Microbiology, 2008, p. 7329-7337.*
Bergel et al, "DSA to grow electrochemically active biofilms of Geobacter sulfurreducens", Oct. 7, 2007.*
International Search Report for PCT/FR2009/050990.
Hasvold et al, "Sea-water battery for subsea control systems", 1997, vol. 65, pp. 253-261, Journal of Power Sources.

* cited by examiner

PRODUCTION OF A BIOFILM ON AN ELECTRODE FOR A BIOCELL, ELECTRODE AND BIOCELL OBTAINED

The present invention relates to a process for producing a biofilm on the surface of an electrode in a medium containing bacteria, to the use of this electrode in a biofuel cell and to the production of electricity using such a biofuel cell.

Very schematically, fuel cells implement an oxidation-reduction reaction, recovering part of the energy, other than heat, given off by this reaction. It is possible to mention, as an example, the hydrogen fuel cell in which a well-known oxidation-reduction reaction occurs:

$$\tfrac{1}{2}O_2 + H_2 \rightarrow H_2O.$$

This is in fact a controlled combustion of the hydrogen and oxygen. The reaction occurs within a structure essentially comprising two electrodes, the anode and the cathode, separated by an electrolyte. The anode chamber is fed with hydrogen and the cathode chamber with oxygen. At the anode the hydrogen is oxidized in the presence of water to give protons according to the reaction:

$$2H_2O + H_2 \rightarrow 2H_3O^+ + 2e^-.$$

The protons then cross the electrolyte under the action of the electric field and the electrons flow through the external circuit of the fuel cell before rejoining the cathode and reducing the dioxygen into water according to the reaction:

$$\tfrac{1}{2}O_2 + 2H_3O^+ + 2e^- \rightarrow 3H_2O.$$

A flow of electrons then passes through the anode so as to travel as far as the cathode and thus creates an electric current.

MFCs (microbial fuel cells) are electrochemical cells that use bacteria to produce electricity, generally from waste water. More commonly called "biofuel cells" their mode of operation is quite similar to that of a conventional fuel cell. The metabolism of the bacteria and the substrate degradation also proceed by a series of oxidation-reduction reactions. Part of the energy produced by these reactions is recovered in biofuel cells which produce an electric current.

Conventionally, biofuel cells consist of two chambers, each containing an electrode (the anode or the cathode), separated by an electrolyte, most often an ion-exchange membrane. As in the conventional fuel cell, the cathode chamber is fed with $O_2$ (or air), the protons cross the electrolyte and the electrons flow through the external circuit of the fuel cell, thus allowing the oxygen to be reduced at the cathode.

The bacteria are active in the anode chamber enabling the liberation of protons and electrons. This liberation is the consequence of oxidation-reduction reactions used by the bacteria to extract the energy that they require from the substrates available to them.

The use of expensive catalysts based on rare metals (platinum or gold) has however for a longtime been necessary to catalyze the oxidation-reduction reactions.

The addition of particular oxidizing/reducing bacteria or enzymes to fuel cells has been considered in order to replace rare-metal catalysts. Initial studies were on the use of bacteria capable of producing or regenerating the fuel, for example hydrogen, or of regenerating the reduced form of an electrochemical mediator by extracting electrons from the substrates present. These studies did not however improve the electrochemical efficiency at the electrodes and the use of catalysts remained necessary.

The article by Hasvold et al. "Sea-water battery for subsea control systems", Journal of Power Sources, 65, pages 253-261, (1997) presents a study of batteries with a soluble anode operating in a marine environment. Batteries submerged in seawater had a higher efficiency than batteries operating in the open air. The authors observed the spontaneous formation of a biofilm (the term "biofilm" is understood to mean a film comprising an array of bacteria spontaneously deposited on a surface) on the cathode which, depending on the circumstances, may have a negative or positive effect on the performance of the fuel cell. The biofilm could be the origin of an improvement in the catalysis of the oxygen reduction.

WO 2004/015806 proposes to produce a biofilm before operating the biofuel cell. The device is a system consisting of three electrodes—a working electrode, a saturated calomel reference electrode and an auxiliary electrode—and a potentiostat which controls the potential difference between the working electrode and the reference electrode and which measures the current between the working electrode and the auxiliary electrode. Depending on the potential difference applied to the working electrode, the latter acts as cathode or anode. The process described is very dependent on the potentials, regulated by the potentiostat, at the working electrode.

Now, during the polarization and production of a biofilm on the working electrode, a biofilm also forms on the auxiliary electrode and on the reference electrode and this biofilm tends to passivate these electrodes. This passivation may modify the potential at the working electrode and may even short-circuit the system.

It has now been discovered that selection of the bacteria responsible for the anodic or cathodic catalysis depends only on the polarization of the electrodes and on the strength of the electric fields that are applied and not on the potentials at the working electrodes.

This discovery makes it possible to provide a process for preparing a biofilm based on a much more flexible and less expensive device than that described in WO 2004/015806.

It consists in simply applying a potential difference between two electrodes that may have the same nature. A simple electric generator is enough. This device uses no reference electrode or auxiliary electrode (generally made of platinum). One of the two electrodes acts as anode and the second acts as the cathode.

This device thus enables a biofilm able to catalyze the oxidation of organic substrates to be selected on the anode. It also enables a biofilm capable of catalyzing the reduction of the oxygen to be selected on the cathode. This device is well suited to industrial application in that it is an easily installed system and it enables to avoid the use of a reference electrode, an auxiliary electrode and a potentiostat.

One subject of the present invention is thus a process for producing a biofilm on the surface of an electrode (or an electrode coated with a biofilm) in a liquid medium containing bacteria and a substrate allowing the bacteria to grow, in which a system of electrodes is used that consists of two electrodes which are connected to a DC current source, these two electrodes are placed in the medium and a predetermined constant potential difference is applied between the electrodes, thereby forming biofilms on the surface of the electrodes.

Another subject of the present invention is a process for preparing a biofuel cell, in which an electrode coated with a biofilm is prepared according to the process for producing a biofilm, and then said electrode is used in a biofuel cell as either anode or cathode.

The invention also relates to a process for producing electricity using a biofuel cell, in which an electrode coated with a biofilm is prepared according to the process for producing a biofilm, and then said electrode is used in a biofuel cell as anode or cathode.

In a preferred embodiment of the process for producing a biofilm, the process aims to form a biofilm on the surface of the anode.

Remarkably, the process of the invention makes it possible to obtain an anode coated with a biofilm having an electron-withdrawing effect when it is transferred to and/or used in a MFC biofuel cell.

According to one feature of the invention, the current source is a current generator. This generator may have a fixed or adjustable set point, however the potential difference or voltage applied is imposed, predetermined and constant over the length of time that it is applied.

According to another feature of the invention, different predetermined potential differences can be successively applied, for example increasing or decreasing potential differences, each being constant over the length of time that it is applied.

In the process according to the invention, the medium containing the bacteria is a static or flowing medium. In a preferred embodiment according to the invention, the medium is static. The term "static" is understood, in the present invention, to mean that during the preparation of the biofilm the medium bathing the electrode remains static and is especially neither stirred nor made to flow.

One subject of the present invention is more particularly a process in which the potential difference applied is between about 100 mV and about 700 mV, preferably between about 300 mV and about 600 mV and more preferably between about 450 mV and about 550 mV. According to one typical embodiment, the potential difference is about 500 mV.

The liquid medium employed to prepare the biofilm contains bacteria and an organic substrate allowing the bacteria to grow. This organic substrate may be located in the liquid medium and/or be supplied to it. Among usable liquid media, nonlimiting examples that may be mentioned include industrial effluents, domestic effluents, agricultural effluents, waste water, water and sludge from wastewater treatment plants, biomass from the food processing industry, natural water (fresh water or salt water), etc.

This medium may also be the same medium in which the biofuel cell will operate so as to produce electricity, once the biofilm has been prepared.

The length of time the potential difference is applied between the electrodes may vary within certain proportions and depending on the medium concerned. This length of time must be sufficient to obtain the biofilm. The formation of the biofilm may be controlled in the following way:
  either producing electricity by removing the voltage;
  or by accumulating bacteria on the anode.

In one embodiment according to the invention, the length of time the potential difference is applied is between about 3 and about 20 days, preferably between about 4 and about 7 days.

The anode, the cathode or even both electrodes may be based on carbon. A material "based on carbon" especially means graphite or a carbon-fiber or carbon-paper material, or reticulated glassy carbon. Other materials may be used, for example: stainless steel, aluminum or nickel, or titanium alloys. Preferably, these materials are chosen in a form having a high specific surface area. Thus, when graphite is used, the electrode or electrodes may be in the form of graphite plates, granules or rods. According to one embodiment of the invention, the two electrodes have the same nature.

It is simplest to prepare the biofilm or biofilms in a vat or the like. It may nevertheless be advantageous to carry out this preparation directly in the biofuel cell, especially when it is desired to use the two electrodes thus prepared.

According to one feature, the process for producing a biofilm is carried out in a dual-chamber biofuel cell, the separation membrane of which has been removed or is not yet in place. By definition, a dual-chamber biofuel cell comprises a chamber containing the anode, a chamber containing the cathode and a separation membrane that lets protons through it but not bacteria or the organic substrate (the membrane may be a cation-exchange membrane). In the absence of a membrane, there is just one chamber filled with liquid medium.

According to another feature, the process for producing a biofilm is carried out in a single-chamber biofuel cell with an air cathode. By definition, the anode and the cathode are placed in the same chamber filled with the liquid medium, the anode being submerged in the chamber, out of contact with the air, and the cathode being placed on the border with a surface in contact with the liquid medium and a surface in contact with the outside air. As a variant, it is possible to use two electrodes submerged in the chamber, the air cathode in this case no longer being used for the preparation of the biofilm.

The efficiency of an MFC biofuel cell largely depends on the transfer of electrons from the bacterium adhering to the anode. The problem with conventional biofuel cells is that most of the bacteria present in the biofilms are electrochemically inactive, their cell walls and other surface structures not being conductive. The process allows a biofilm rich in high-redox-potential, electron-withdrawing bacteria to be selected at the anode. The redox potential of the biofilm thus obtained, when it is placed under the operating conditions of the biofuel cell, is greater than the redox potential of a normal biofilm produced without applying the process of the invention (that is to say if the MFC biofuel cell is simply placed in contact with the same medium and the redox potential is measured once the biofuel cell has reached its steady state). The redox potential may be measured using cyclic voltammetry (for example with a silver chloride reference electrode). It follows that a biofuel cell employing an anode according to the invention generates more electric power than a biofuel cell the anode of which has not been enriched according to the invention.

Another subject of the present invention is such an anode coated with a biofilm comprising or consisting of high-redox-potential bacteria obtained by implementing the process according to the invention. This biofilm is able to catalyze the oxidation of organic substrates.

Another subject of the present invention is a cathode coated with a biofilm consisting of bacteria capable of catalyzing the reduction of oxygen.

Another subject of the present invention is a biofuel cell comprising an electrode coated with a biofilm and obtained by implementing the biofilm preparation process according to the invention.

In a first embodiment, the biofuel cell contains an anode according to the invention coated with its biofilm conforming to the invention.

In a second embodiment, the biofuel cell contains a cathode according to the invention coated with its biofilm conforming to the invention.

In a third embodiment, the biofuel cell contains an anode and a cathode, according to the invention, coated with their biofilms conforming to the invention.

According to one embodiment, the biofuel cell is a double-chamber cell with separation by a membrane. In an advantageous embodiment, the anode, the cathode or both electrodes are prepared in the biofuel cell in the absence of the separation membrane, the latter being added to form the complete biofuel cell.

According to another embodiment, the biofuel cell is a single-chamber cell with an air cathode. In one advantageous embodiment, the anode, the cathode or both electrodes are prepared in the biofuel cell itself.

The biofuel cells thus obtained by implementing the process of the invention are used in facilities for producing electricity from media of various origins containing substrates that can be metabolized by the bacteria present on the surface of the electrode or electrodes. These media may be liquids, for example: industrial effluents, domestic effluents, agricultural effluents, waste water, water and sludge from wastewater treatment plants, biomass from the food processing industry, natural water (fresh water or salt water); or solids, for example: soils, marine or river sediments, etc.

According to one particular embodiment, the device that served for the biofilm preparation forms the biofuel cell itself. In this case, after switching off or disconnecting the current source and optionally adding the separation membrane, if the cell is a dual-chamber biofuel cell, the biofuel cell is used as a current generator.

The configuration of biofuel cells is moreover known to those skilled in the art. These biofuel cells comprise apertures so that the organic-substrate-carrying medium can make contact with the anode. A flow may be provided to ensure this contact.

Another subject of the invention is an electricity production facility comprising one or more biofuel cells as described hereinabove. When a plurality of biofuel cells are present, they may be connected in series or in parallel.

The present invention will be illustrated with the following examples, without however limiting the scope thereof, and by referring to the appended drawings.

EXAMPLE 1

Preparation of a Biofilm on the Anode and on the Cathode

Figure 1:
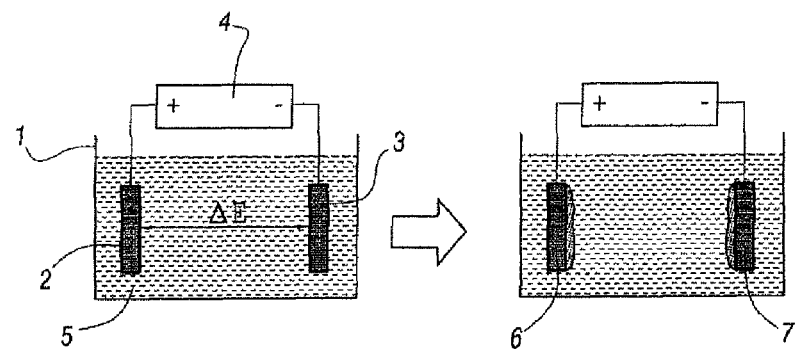
FIG. 1 shows a schematic of an electrochemical device allowing anodic and cathodic biofilms to be produced, the left-hand side of the figure showing the device at start-up and the right-hand side showing the device after a biofilm has been formed on the surface of the electrodes.

The electrochemical device shown in FIG. 1 comprises a vat 1, two similar electrodes (anode 2 and cathode 3) made of graphite and a current generator 4. The vat was filled with waste water 5 from a domestic-waste water treatment facility.

Using the generator 4, a voltage of 0.5 V was applied for 4 days. The left-hand side of FIG. 1 shows the device at start-up and the right-hand side shows the device after 4 days, with a biofilm 6 formed on the anode and a biofilm 7 formed on the cathode.

For comparison, a similar device was left for 4 days without applying a voltage (unpolarized electrodes).

Next, the cyclic voltammograms of the biofilms formed on the anode, on the cathode and on an unpolarized electrode were determined in a phosphate buffer (0.1M, pH=7). To do this, voltammetry was carried out using a conventional device having three electrodes, one of which was a silver chloride reference electrode.

Figure 2:
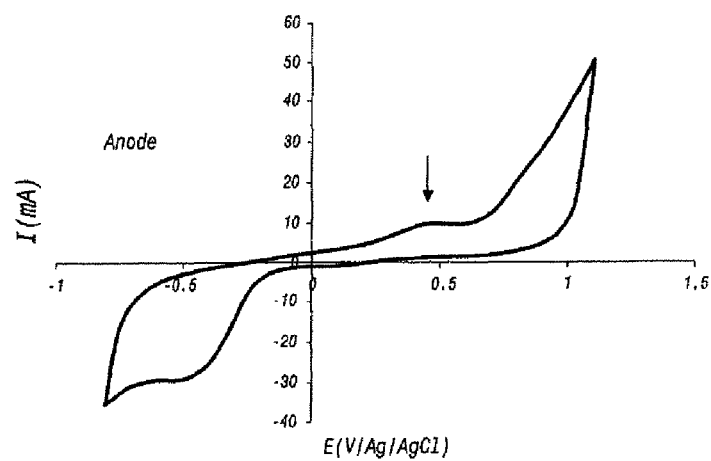
FIG. 2 is a cyclic voltammogram, in a phosphate buffer (0.1M, pH=7), of a biofilm formed on the anode.
Figure 3:
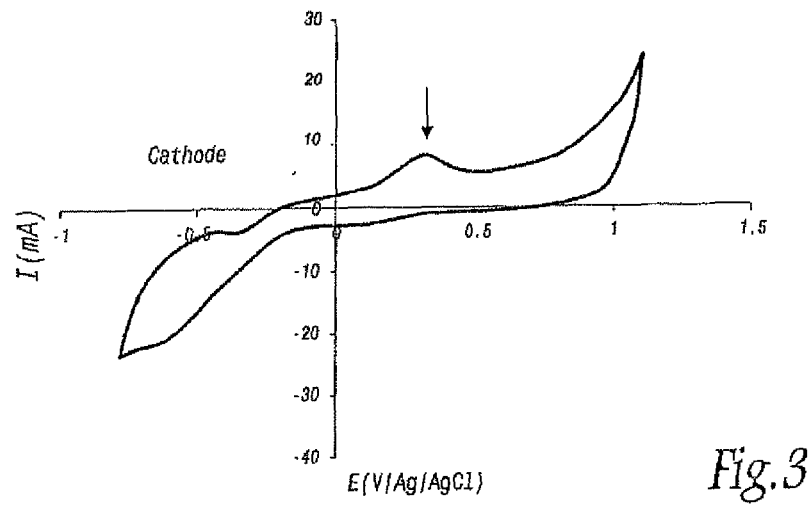
FIG. 3 is a cyclic voltammogram, in a phosphate buffer (0.1M, pH=7), of a biofilm formed on the cathode.
Figure 4:
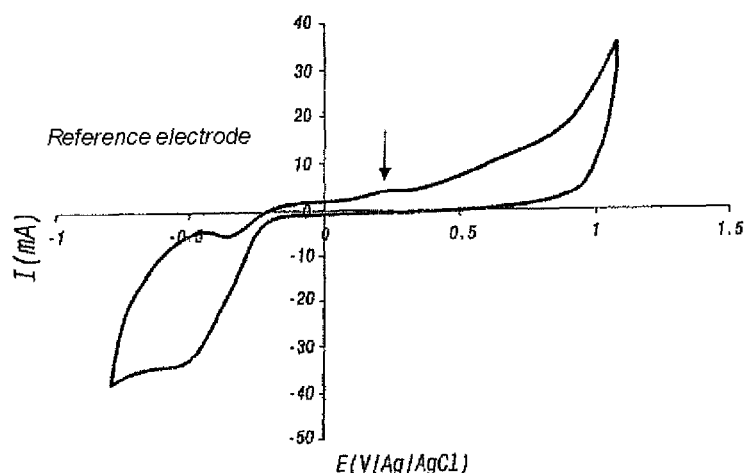
FIG. 4 is a cyclic voltammogram, in a phosphate buffer (0.1M, pH=7), of a biofilm formed on an unpolarized reference electrode.
Figure 5:
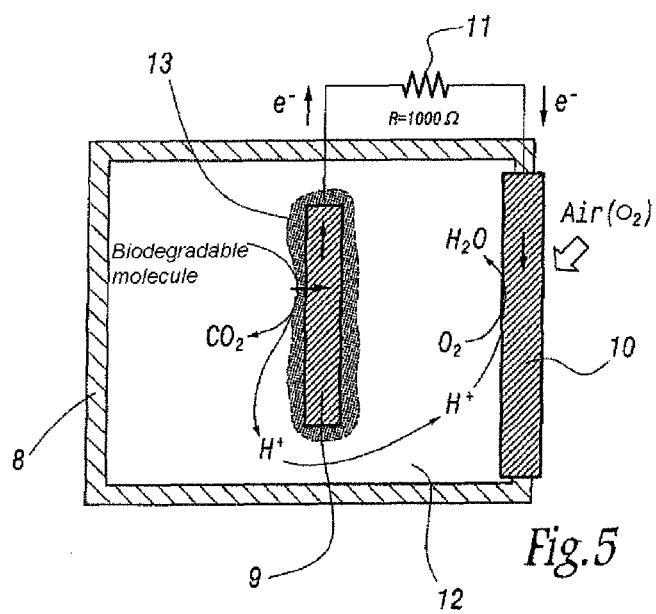
FIG. 5 shows a schematic of a biofuel cell.

Comparing the voltammograms clearly shows that biofilms having different electrochemical activities were obtained (FIGS. 2, 3 and 4). The positive potential peak of the anodic biofilm is located at about 0.46 V/Ag/AgCl and is larger than those observed for the cathode (0.31 V/Ag/AgCl) and for the unpolarized electrode (0.25 V/Ag/AgCl). The variation of the position of the anodic peaks reflects the potential-energy difference between the microbial electron donors, such as redox proteins, of each biofilm and demonstrates that, according to the invention, a positive polarization of an electrode during the formation of a biofilm allows this film to be enriched with high-redox-potential bacteria.

EXAMPLE 2

Biofuel Cell

An air-cathode biofuel cell was used. It comprised a tank 8 containing an anode 9 and a cathode 10 placed level with a wall of the tank so as to have one surface turned toward the inside of the tank and one surface turned toward the outside, in contact with the air. An electrical circuit was formed connecting the electrodes and comprising a resistor 11—the voltage of the biofuel cell was measured at the terminals of this resistor using a measurement device (not shown).

The tank 8 and the cathode 10 defined a chamber which was filled with a minimum nutrient solution: a PBS (phosphate buffer solution), namely $Na_2HPO_4$ (4.1 g/l), $NaH_2PO_4, H_2O$ (2.9 g/l), $NH_4Cl$ (0.3 g/l), KCl (0.1 g/l); and an acetate substrate (>1.0 g/l).

Two biofuel cells were thus prepared, one in which the anode was an anode prepared according to example 1 and covered with a biofilm 13, the other in which the anode had not been pretreated.

Figure 6:
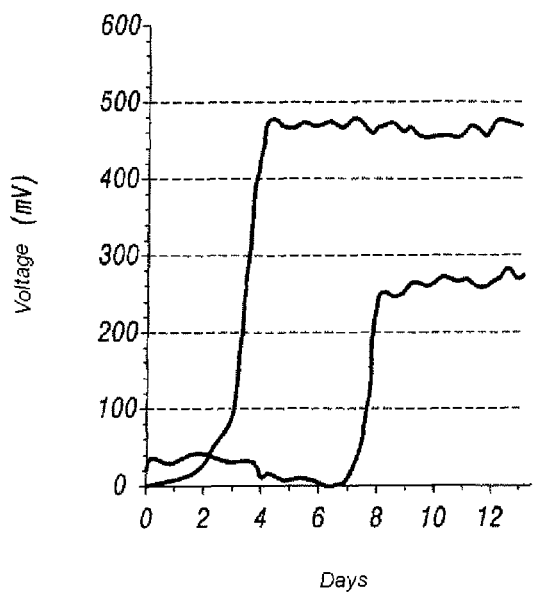
FIG. 6 is a graph showing the voltage of a biofuel cell according to the invention compared with a biofuel cell without anodic pretreatment, as a function of time.

FIG. 6 is a graph showing the voltage of these biofuel cells as a function of time. The curve showing an earlier appearance of a voltage across the terminals and a higher plateau corresponds to the biofuel cell equipped with an anode having a biofilm, obtained according to example 1. A voltage develops very quickly with the biofuel cell according to the invention. Likewise, the maximum voltage of about 470 mV is much higher than the 270 mV of the biofuel cell without the anode pretreatment. These results demonstrate that the formation of a biofilm on the anode, according to the invention, by positively polarizing the anode, clearly improves the performance of a biofuel cell by virtue of electrochemical enrichment in efficient bacteria of the biofilm.

The invention claimed is:

1. A process for producing a biofilm on the surface of an electrode in a liquid medium containing bacteria and a substrate allowing the bacteria to grow, comprising using a system of electrodes that consists of two electrodes wherein both electrodes are connected to a DC current source, placing these two electrodes in the medium and applying a predetermined constant potential difference between the electrodes, thereby forming biofilms on the surface of the electrodes, wherein the formed biofilm is rich in hi h-redox potential, wherein electron-withdrawing bacteria is produced at the anode and wherein the process does not use a membrane, and wherein the potential difference applied is between 100 mV and 700 mV.

2. The process as claimed in claim 1, in which the potential difference applied is between 300 mV and 600 mV.

3. The process as claimed in claim 1, in which the potential difference applied is between 450 mV and 550 mV.

4. The process as claimed in claim 1, in which the potential difference is applied for a length of time of between 3 and 20 days.

5. The process as claimed in claim 4, in which this length of time is between 4 and 7 days.

6. The process as claimed in claim 1, in which the electrodes are made from the same material.

7. The process as claimed in claim 6, in which the anode and/or the cathode are/is based on carbon and/or stainless steel, aluminum, nickel or on titanium alloys.

8. A process for preparing a biofuel cell comprising the preparation of an electrode according to the process as claimed in claim 1 and then the use of this electrode in a biofuel cell as either anode or cathode.

9. A process for producing electricity, in which a biofuel cell such as that obtained in claim 8 is used.

10. An electricity production facility comprising one or more biofuel cell(s) prepared according to claim 8.

11. An electrode coated with a biofilm that can be obtained by implementing the process as claimed in claim 1.

12. An anode coated with a biofilm, containing oxidizing/reducing bacteria, that can be obtained according to claim 1.

13. A biofuel cell comprising an electrode obtained by implementing the process as claimed claim 1.

14. A biofuel cell comprising an anode as claimed in claim 12.

15. A process according to claim 1 wherein the liquid medium is selected from the group consisting of industrial effluents, domestic effluents, agricultural effluents, waste water, water and sludge from wastewater treatment plants, biomass from the food processing industry, and natural water.

* * * * *